United States Patent [19]

Sekido et al.

[11] Patent Number: 4,601,883

[45] Date of Patent: Jul. 22, 1986

[54] SENSOR ELEMENT

[76] Inventors: Satoshi Sekido, 53-10, Kurigatani, Hashimoto, Yawata-shi, Kyoto; Hirokazu Tachibana, 151-16, Ninomaru-cho, Mukaijima, Fushimi-ku, Kyoto-shi, Kyoto; Yoshito Ninomiya, 1-9-4, Nasuzukuri, Hirakata-shi, Osaka, all of Japan

[21] Appl. No.: 741,209

[22] Filed: Jun. 5, 1985

Related U.S. Application Data

[63] Continuation of Ser. No. 331,325, Dec. 16, 1981, abandoned.

[30] Foreign Application Priority Data

| Dec. 19, 1980 [JP] | Japan | 55-180690 |
| Jun. 12, 1981 [JP] | Japan | 55-91178 |
| Jun. 12, 1981 [JP] | Japan | 56-91179 |
| Jun. 12, 1981 [JP] | Japan | 56-91180 |

[51] Int. Cl.$^4$ ............................................. G01N 27/04
[52] U.S. Cl. .................................... 422/94; 73/23; 338/34; 422/98; 502/303
[58] Field of Search ............... 73/23, 27 R; 324/71.5; 338/34; 422/94, 98; 502/303

[56] References Cited

U.S. PATENT DOCUMENTS

| 3,900,428 | 8/1975 | Mai et al. | 252/462 |
| 3,901,828 | 8/1975 | Mai et al. | 252/462 |
| 3,951,603 | 4/1976 | Obayashi et al. | 23/232 E |
| 4,049,583 | 9/1977 | Lauder | 423/213.2 |
| 4,221,827 | 9/1980 | Parry et al. | 422/98 |
| 4,314,996 | 2/1982 | Sekido et al. | 422/98 |

Primary Examiner—Barry S. Richman
Assistant Examiner—Michael S. Gzybowski

[57] ABSTRACT

A sensor element comprising a substrate made of a compound oxide of the perovskite type, the compound oxide having the formula $A_{1-x}A'_xB_{1-y}B'_yO_3$ in which A represents a trivalent element selected from the group consisting of La, Ce, Pr and Nd, A' represents a divalent element selected from the group consisting of Ca, Sr and Ba, B represents equal amounts of trivalent and tetravalent Co, B' represents a tetravalent element selected from the group consisting of Fe, Mn, V and Ti, x has a value ranging from (0.6) to (0.95) and y has a value ranging from (0.2) to (0.9) with the proviso that x must equal $\frac{1}{2}(1+y)$.

5 Claims, 17 Drawing Figures

SENSOR ELEMENT

This application is a continuation of application Ser. No. 331,325, filed Dec. 16, 1981, now abandoned.

BACKGROUND OF THE INVENTION

Field of the Invention

This invention relates to the detection of gases and more particularly, to a sensor element and method for making such a sensor element. More specifically, the present invention relates an improvement of an oxygen sensor proposed in our copending U.S. patent application No. 136,404, now U.S. Pat. No. 4,314,996 dated Feb. 9, 1982.

In the U.S. patent application, we have proposed an oxygen sensor which comprises a substrate made of perovskite compounds of the formula, $ABO_3$, in which A represents an element of a lanthanum family, an alkaline earth metal or a mixture thereof and B represents a transition metal. This type of perovskite compound can serve as a catalyst for combustion and has such a characteristic that its electrical resistance abruptly varies in the vicinity of a stoichiometric point of combustion of both types of gases when applied as a sensor element.

Further, there have also been proposed gas sensor elements for detecting reducing gases and vapors such as alcohols or carbon monoxide or for determining oxygen concentration such as, for example, in U.S. Pat. No. 3,951,603. The sensor element of this patent makes use of a complex metal oxide of a perovskite crystal structure of the general formula $A_{1-x}A'_xBO_{3-\delta}$ represents at least one element such as a rare earth metal, yttrium or hafnium, A' represents at least one element such as an alkaline earth metal or lithium, B is at least one element such as a transition metal, x is in the range of $0 \leq x \leq 1$, and $\delta$ is a non-stoichiometricx parameter. This sensor element is applied to an atmospheric gas composition which has a large partial pressure of oxygen and its operation mechanism is substantially the same as that of gas sensors using ordinary oxide semiconductors.

Among various types of perovskite compounds, compounds which contain cobalt (Co) in the B site of the above formulas have experimentally been confirmed to show very low resistance in an oxidizing gas-rich atmosphere. In addition, the Co-containing compounds show abrupt variation in resistance in the vicinity of an equivalence or stoichiometric point of both types of gases and are thus very useful as a material for gas sensor element. However, this type of perovskite compound is disadvantageous in that once exposed to an atmosphere where reducing gases are rich or in excess, the compound does not become low in resistance even after the atmosphere has been changed to an oxidizing gas-rich atmosphere. Additionally, long-term exposure to a reducing gas atmosphere may result in breakage in structure of the perovskite compound.

SUMMARY OF THE INVENTION

Accordingly, an object of the invention is to provide a sensor element which has a catalytic function of causing the chemical equilibrium reaction (combustion reaction) to proceed rapidly in an atmospheric gas where oxidizing gases such as NOx, SOx and $O_2$ and reducing gases such as hydrocarbons, CO, alcohols, $H_2$ and the like coexist.

Another object of the invention is to provide a sensor element whose substrate is made of a compound oxide of the perovskite type which contains cobalt as one of the metal components but overcomes the disadvantages of known similar compounds.

A further object of the invention is to provide a sensor element whose resistance abruptly varies at the equivalence point of an inflammable gas composition, i.e. the resistance becomes high in an atmosphere where reductive gases are rich and low in an atmosphere where oxidative gases are rich.

A still further object of the invention is to provide a sensor element which is excellent in responsibility and long in lifetime.

Another object of the invention is to provide a method for making the sensor element of the just-mentioned type.

The above objects can be achieved according to the invention by a sensor element which comprises a porous substrate made of a compound oxide of the perovskite type and a pair of electrodes electrically connected to the substrate in a spaced relation with each other, the compound oxide having the formula $A_{1-x}A'_xB_{1-y}B'_yO_3$ in which A represents at least one element selected from the group consisting of lanthanides including La, Ce, Pr and Nd, A' represents at least one element selected from the group consisting of Ca, Sr and Ba, B represent Co, B' represents at least one element selected from the group consisting of Fe, Mn, V and Ti, x is a value ranging from 0.6 to 0.95 an y is a value ranging from 0.2 to 0.9 provided that an atomic ratio of the element A' is equal to the sum of an atomic ratio of the element B' and a half of an atomic ratio of the element B or $x = \frac{1}{2}(1+y)$.

The sensor element can be made by a method which comprises mixing an aqueous solution of the elements A, A', B and B' each in the form of a water-soluble nitrate, acetate or oxalate except that an oxide powder is used when V and/or Ti is used as the B' element, thermally decomposing the water-soluble salts, heating the decomposition products at a temperature of 850° to 1050° C. to give a powder of a compound oxide of the perovskite type, adding to the powder an aqueous solution of 20 to 40% methyl cellulose based on the powder, drying the mixture to a moisture content of below 45 vol. %, press-molding the mixture in a given form, and sintering the resulting molding at a temperature of 1000° to 1200° C. The pair of electrodes is usually attached to the substrate or molding at the time of the press molding operation.

EMBODIMENTS OF THE INVENTION

Figure 1A:
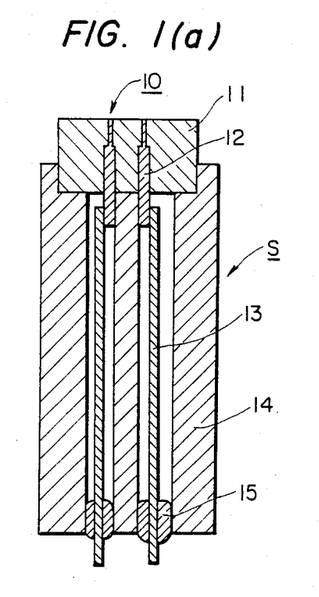
FIGS. 1(a) and 1(b) are, respectively, schematic plan and side views, in section, of a sensor according to one embodiment of the invention.
Figure 1B:
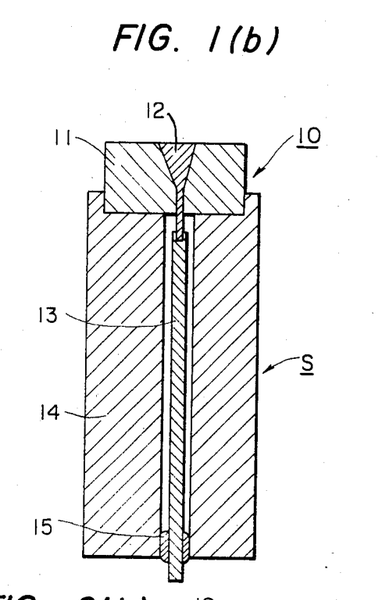

Referring now to the accompanying drawings and particularly to FIGS. 1(a) and 1(b), there is shown a sensor S of a pellet type according to one embodiment of the invention. The sensor S includes a sensor element 10 having a substrate 11 and a pair of metallic wires 12, each serving as an electrode and lead, in a spaced relation as shown. In order to prevent each lead 12 from being readily removed from the substrate 11, it is made flat at the top portion thereof. The leads 12 are each electrically connected to a heat-resistant metal lead 13 which is accommodated in a ceramic tube 14. The lead 13 is fixed to the tube 14 by means of a ceramic cement 15.

Figure 2A:
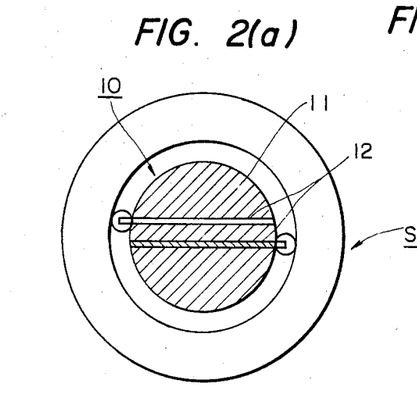
FIGS. 2(a) and 2(b) are, respectively, top and partially sectional side views of a sensor according to another embodiment of the invention.
Figure 2B:
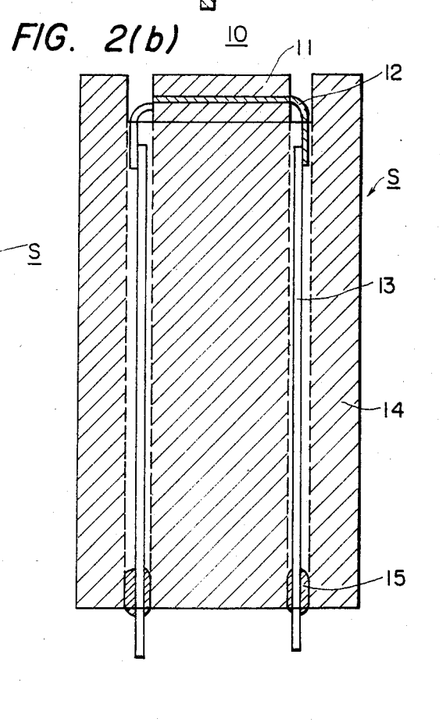

FIGS. 2(a) and 2(b) show another embodiment of the invention in which the metallic wires 12 are attached in a manner different from the first embodiment of FIGS. 1(a) and 1(b). It will be noted that in these figures, like reference numerals identify like parts.

The sensors of FIGS. 1 and 2 exhibit little differences in characteristics therebetween and the sensor shown in FIGS. 2(a) and 2(b) is used to illustrate the characteristics thereof. The sensor used has a diameter of 4 mm, a thickness of 2.5 mm, an outer diameter of an electrode and lead wire of 0.3 mm and a distance between the wire centers of 1.00 mm.

The sensor is placed in a tubular furnace held at 850° C. and then subjected to a repeated cycle wherein an $N_2$ gas containing 100 ppm $O_2$ is initially passed and then an $N_2$ gas containing 100 ppm CO is passed. The passage of each gas is continued for 1 hour in every cycle.

Figure 3A:
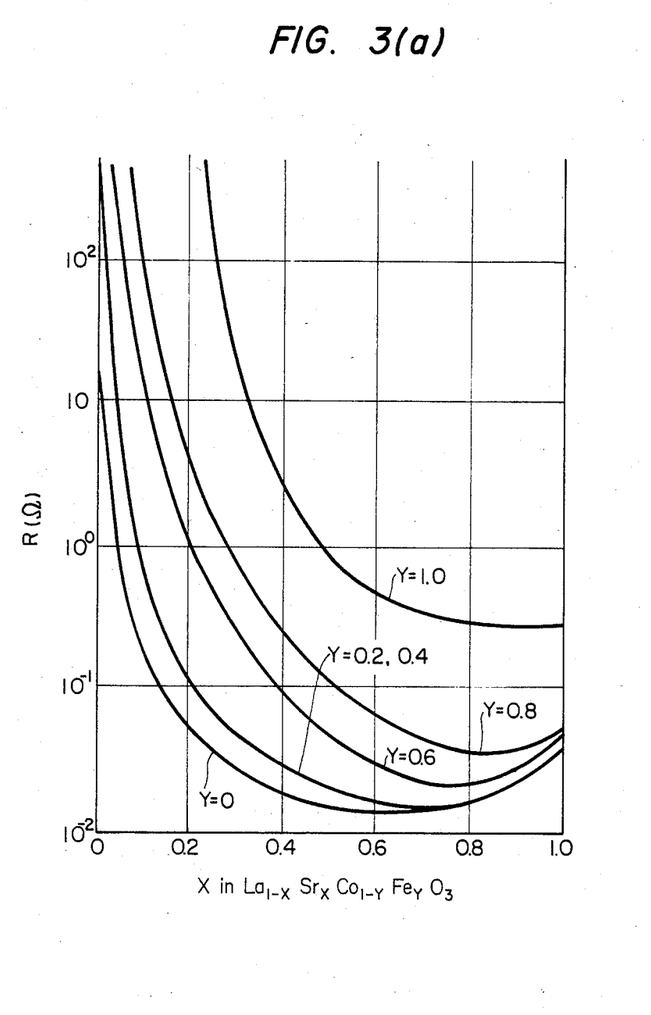
FIGS. 3(a) and 3(b) are, respectively, graphical representations of the steady state resistance in $O_2$-containing and CO-containing $N_2$ gas atmospheres in relation to the variation in value of x in $La_{1-x}Sr_xCo_{1-y}Fe_yO_3$ for different values of y.
Figure 3B:
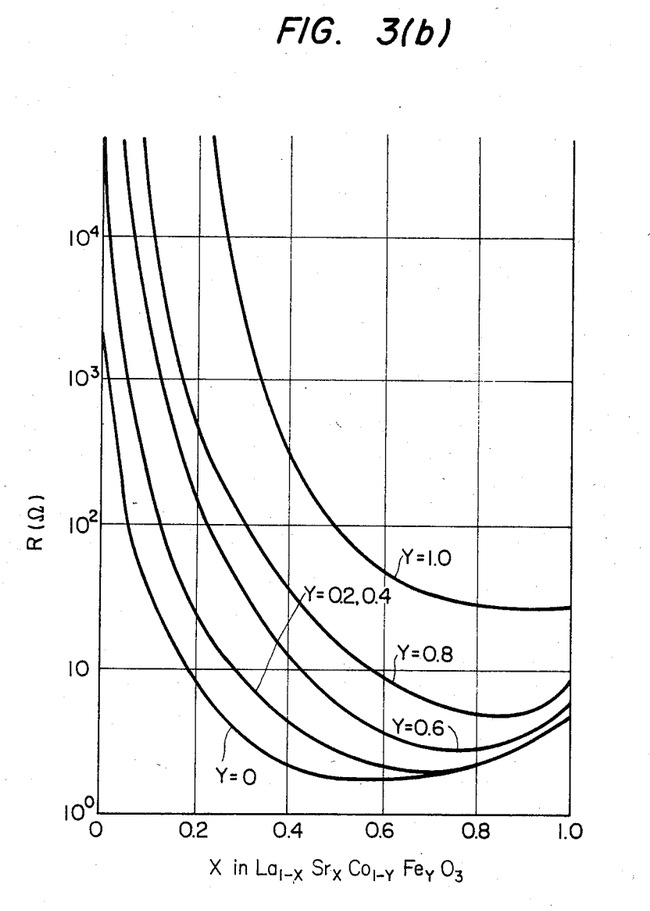

FIGS. 3(a) and 3(b) show steady state resistance values of a sensor using a compound oxide of the formula $A_{1-x}A'_xB_{1-y}B'_yO_3$ in which A is La, A' is Sr, B is Co and B' is Fe, in atmospheres of $N_2$ gas containing 100 ppm $O_2$ and 100 ppm CO, respectively. It has been found that the resistance of the sensor is not dependent on the type of the element A even when elements other than La, including Ce, Pr and Nd, are used. This is true of the element A' provided that the composition of the B site satisfies the requirement that y is in the range of 0.2 to 0.9. Accordingly, similar results are obtained when Ca or Ba is used instead of Sr. As for the element B', the resistance increases in the order of Fe<Mn<V<Ti but the variation in resistance is almost at the same level.

Figure 4:
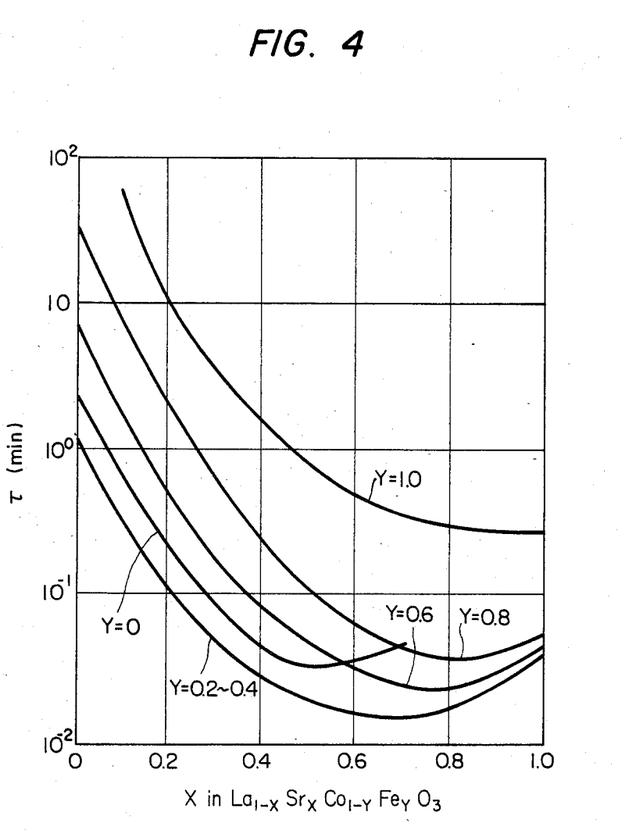
FIG. 4 is a graphical representation of the response time of the same sample as used with regard to FIGS. 3(a) and 3(b) at the time when the atmosphere is changed from an oxygen-rich state to a CO-rich state.

FIG. 4 shows a response time $\tau$ which is obtained when the atmosphere is changed from an oxygen-rich state (a stream of $N_2$ gas containing 100 ppm $O_2$) to a CO-rich state (a stream of $N_2$ gas containing 100 ppm CO). The response time is expressed by a time required for a variation by 90% of the difference between the steady state resistances in the respective types of atmospheres. The same sensor as used with reference to FIGS. 3(a) and 3(b) is employed in this case. The order of the response time is the same as an order of a gas disappearance speed in case where a mixture of CO and $O_2$ in an equivalent ratio is passed over the sensor sample. In general, the response speed in the case where a CO-rich gas is changed to an $O_2$-rich gas is much larger than in the case of FIG. 3(b) (see FIG. 9).

The sensor element according to the invention greatly varies in resistance at the equivalence point of combustion. Taking the variation in resistance (FIGS. 3(a) and 3(b)) and the response time (FIG. 4) into account, the composition of the compound oxide is generally in the ranges of y=0.2-0.9 and x=0.6-0.95, and when the CO-containing atmosphere is used as a reductive atmosphere, it is preferred that y=0.2-0.4 and x=0.6-0.7.

Figure 5:
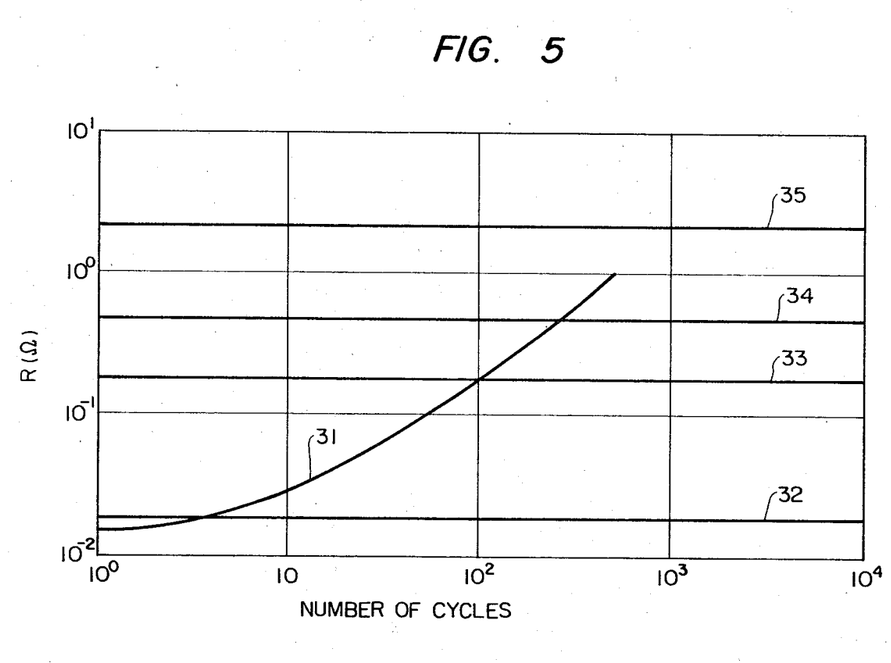
FIG. 5 is a graphical representation of the resistance in an atmosphere of 100 ppm of $O_2$ and the balance of $N_2$ in relation to the repetition of a cycle where an atmospheric gas is changed every hour between an oxidative gas containing 100 ppm $O_2$ and a reductive gas containing 100 ppm CO (the balance being $N_2$) for different compositions of the perovskite-type compound oxide.

The effects of the element B' are shown in FIG. 5. In the figure, by 31 is indicated a variation in resistance of $La_{0.5}Sr_{0.5}CoO_3$, by 32 is a similar variation of $La_{0.4}Sr_{0.6}Co_{0.8}Fe_{0.2}O_3$, by 33 is a similar variation of $La_{0.4}Sr_{0.8}Mn_{0.2}O_3$, by 34 is a similar variation of $La_{0.4}Sr_{0.6}Co_{0.8}V_{0.2}O_3$, and by 35 is a similar variation of $La_{0.4}Sr_{0.6}Co_{0.8}Ti_{0.2}O_3$, all the variations being obtained when the sensors are placed in a stream of $N_2$ gas containing 100 ppm $O_2$. When no B' element is added, the resistance of the sensor increases in two steps at the time when a $N_2$ gas containing 100 ppm CO is passed for 1 hour, and the resistance in an atmosphere of $N_2$ gas containing 100 ppm $O_2$ tends to gradually increase. However, the addition of the B' element results in a remarkable improvement of reproducibility.

Figure 6A:
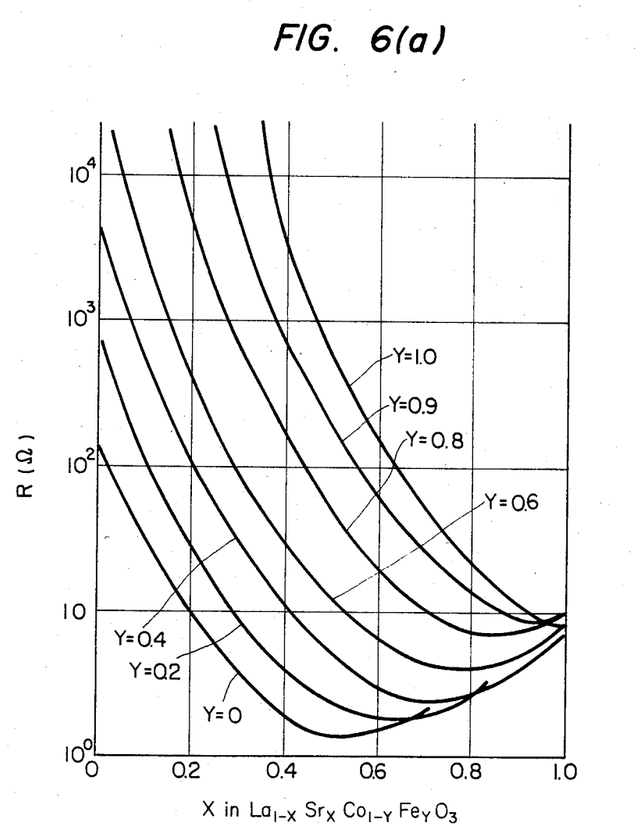
FIGS. 6(a) and 6(b) are, respectively, graphical representations of the resistance in a 100 ppm i-$C_4H_{10}$-containing $N_2$ gas atmosphere and the response time required for a variation by 90% of a difference between the steady state resistance values in both types of gases.
Figure 6B:
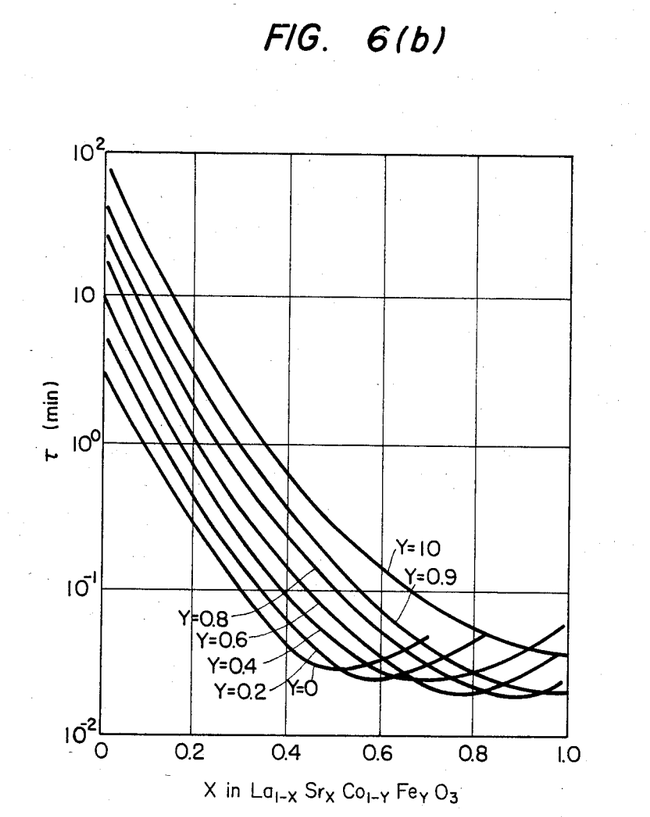
Figure 7A:
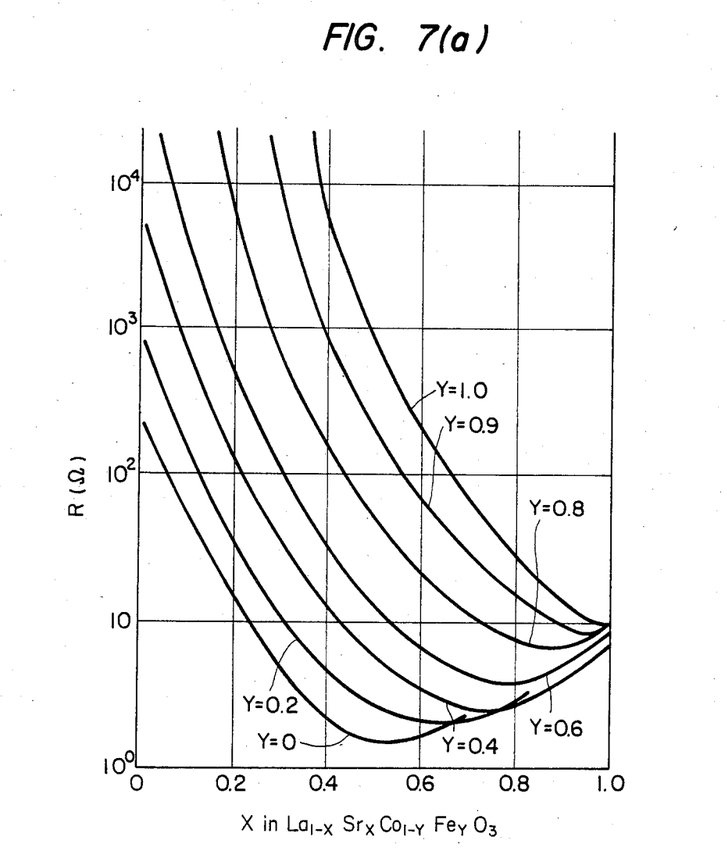
FIGS. 7(a) and 7(b) are, respectively, similar to FIGS. 7(a) and 7(b) but 100 ppm $H_2$ is used instead of i-$C_4H_{10}$.
Figure 7B:
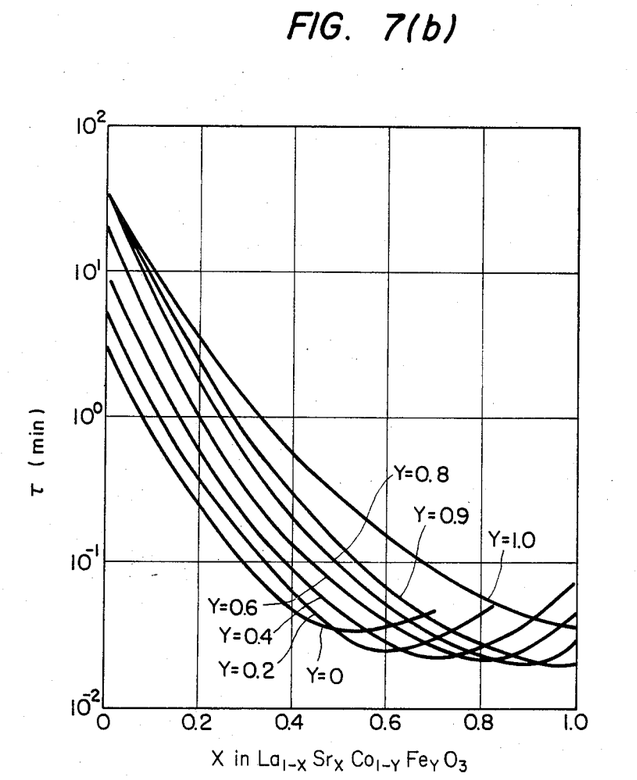

A sensor of the same type as used with reference to FIGS. 3(a) and 3(b) is placed in streams of $N_2$ gas containing 100 ppm i-$C_4H_{10}$ and $H_2$ to determine a steady state value of resistance and a response time in the respective gas atmospheres. FIGS. 6(a) and 6(b) show the resistance and the response time in the i-$C_4H_{10}$-containing $N_2$ gas atmosphere, respectively, and FIGS. 7(a) and 7(b) similarly show the resistance and the response time in the $H_2$-containing $N_2$ gas atmosphere. As will be seen from the figures, the sensor in the atmospheres containing i-$C_4H_{10}$ and $H_2$ shows a tendency slightly different from the case in the CO-containing atmosphere. That is, when the atomic ratio y of Fe in the B site is 0.9 and x is 0.95, the variation in resistance becomes maximal and the responsibility becomes high. Accordingly, when i-$C_4H_{10}$ and $H_2$ are rich in atmosphere, the optimum values of y and x are 0.9 and 0.95, respectively.

The resistance value in an oxidative gas-rich atmosphere greatly varies depending on the amount of Sr in the A site as is apparently seen in FIG. 3(a) but the minimal value of resistance depends on the amount Fe in the B site. That is, the minimal resistance is obtained when the sum of the atomic ratio of the element B' and a half of the atomic ratio of Co is equal to the atomic ratio of the element A'. Assuming that the substituted elements B' in the B site such as Fe, Mn, V and Ti are incorporated as a tetravalent element, it is meant that tri- and tetra-valent Co coexist in equal amounts. When a sensor made of a compound oxide of the perovskite type containing cobalt is exposed to a reductive gas, it serves as an $O^{2-}$ ion doner and thus the deficiency of oxygen increases and tetravalent cobalt is so reduced in amount that the resistance increases. When tetravalent Co completely disappears and is converted into divalent Co, the crystalline structure is changed. With $Sr_xLa_{1-x}CoO_3$, the conversion reaction is not reversible as is known in the art. The substitution of a part of Co with Fe, Mn, V or Ti is believed to contribute to prevent formation of divalent Co.

The practical effect of the sensor element according to the invention which is applied to a gas burner is described.

Figure 8:
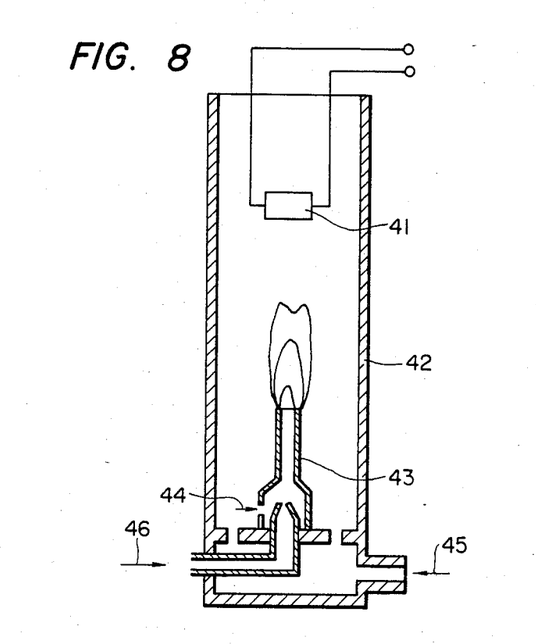
FIG. 8 is a schematic view of a sensor according to the invention applied to a combustion device.
Figure 9:
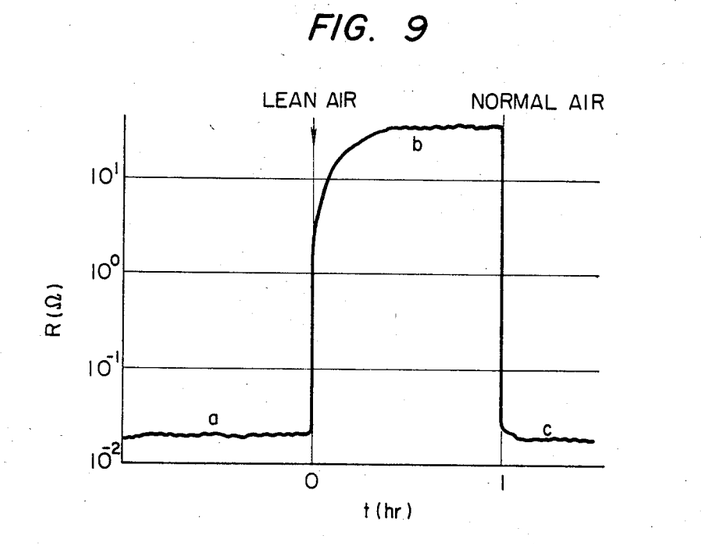
FIG. 9 is a graphical representation of the resistance of the sensor of FIG. 8.

A sensor substrate made of $La_{0.4}Sr_{0.6}Co_{0.8}Fe_{0.2}O_3$ which shows the great effect in the foregoing example is used. FIG. 8 shows a device used in this experiment, in which a sensor 41 according to the invention is placed at the upper portion of a combustion chamber 42 constituted of a stainless steel tube for preventing the flame from flickering under oxygen-lean conditions. At the lower portion of the combustion chamber 42 is provided a Busen burner 43. A primary air vent 45 for the Busen burner 43 and a gas charge port 46 are also provided as shown. The sensor is disposed within the combustion chamber 42 such that it is positioned in the inner flame of the burner when oxygen-lean air is passed. FIG. 9 shows a variation in resistance of the sensor in case where a stream of normal air is passed and then a stream of oxygen-lean air ($O_2$ content of 18%) is passed. The stream is changed from normal air to the lean air every hour.

As will be apparent from the results shown in FIG. 9, the equivalence point of combustion can be detected by means of the sensor according to the invention using no noble metals and thus the sensor can be employed for detecting a concentration of oxygen in air or controlling the combustion. As is clearly seen in FIG. 9, the resistance of the sensor is as low as $10^{-2}\Omega$ in an atmosphere where an oxidative gas in rich and increases abruptly in an atmosphere rich of reductive gas, which can be utilized to control an electromagnetic switchover valve by connecting the sensor in series with an electric source for thermocouple together with the electromagnetic valve. In general, the sensor of the invention is particularly useful in directly controlling an actuator solenoid by connecting the sensor and the selenoid in series to a power circuit, by which the solenoid can be worked in response to its abrupt variation in resistance.

Then, a method of fabricating the sensor element of the invention is described. First, preparation of a powder of a compound oxide of the perovskite type is described. Though oxide powders of the respective metal elements may be used as a starting material for the sensor substrate, it is recommended to conduct the reaction for producing an intended compound oxide of the perovskite type at temperatures as low as possible. This is due to the fact that lower temperatures result in a greater specific surface area of the resulting powder, leading to better responsibility when such powder is applied as a sensor substrate. Accordingly, it is preferable to use a powder of a compound oxide which is obtained by dissolving in water water-soluble salts such as acetates, oxalates or nitrates except that when Ti and/or V is used as an oxide powder. The solution is agitated and evaporated to dryness in suitable means such as a rotary evaporator to obtain a powder, followed by heating the powder in air at temperatures sufficient to decompose and oxidize the salts in the powder. The decomposition temperature is usually about 450° C. as is well known in the art. The resulting product is press-molded in a given form and calcined in air at a temperature of 850° to 1050° C. for a time of 5 to 10 hours to obtain a powder of an intended compound oxide of the perovskite structure. If mixed oxides are used as a starting material, the calcination must be conducted at temperatures higher by 300° C. than the above temperature to obtain a product of a single perovskite structure with fine sizes. To the resulting powder is then added an aqueous solution containing 20 to 40% of methyl cellulose based on the powder, which is subsequently mixed well and heated at 50° C. to remove the water therefrom to such a level that the moisture content is below 45 vol. %. This mixture is molded in a given form and sintered at temperatures below 1200° C., preferably 1000° to 1200° C. for one to several hours. As a consequence, a sensor substrate of a given form can be obtained. Metallic wires serving as a lead and electrode are usually applied to or embedded in the substrate at the time of the molding operation.

As described above, the sensor substrate is preferred to have a greater specific surface area. When the sensor is exposed to an atmosphere where a reductive gas is rich, its resistance increases but such an increase does not take place instantaneously unless all the portions of the substrate lying between the electrodes through which an electric current is passed increase in resistance. It is believed that the portions have to be fine in structure or at least contain a fine structure. The difference in responsibility based on the difference of preparation of the compound oxide of $La_{0.4}Sr_{0.6}Co_{0.8}Fe_{0.2}O_3$ is illustrated. The same experimental conditions as used with reference to FIG. 4 are used.

Figure 10:
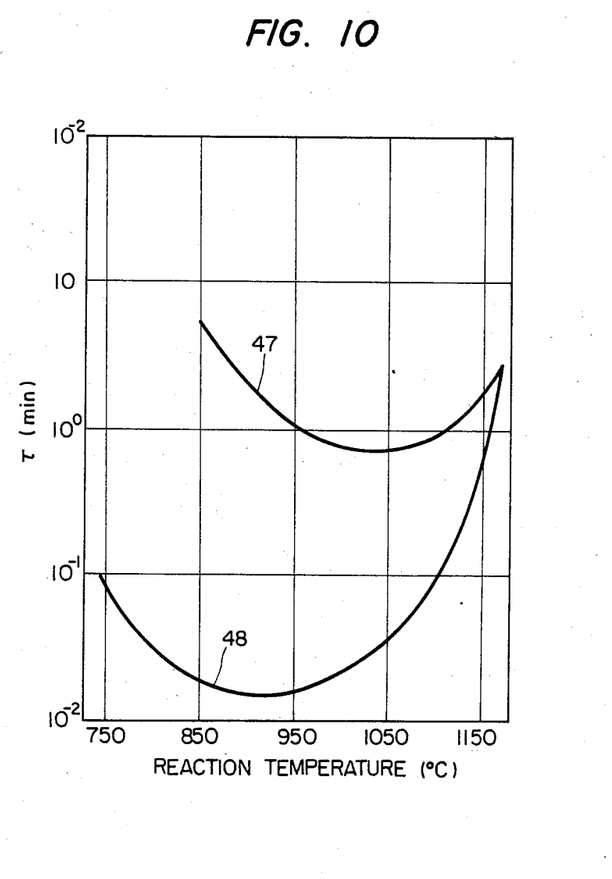
FIG. 10 is a graphical representation of the response time similar to FIG. 4(b) in relation to the variation in reaction temperature at which a starting compound oxide is prepared.

FIG. 10 shows a relation between the reaction temperature at which the compound oxide is prepared and the response time, in which by 47 indicated is a sensor using the compound oxide prepared from starting oxide powders and by 48 is a sensor using the compound oxide prepared from water-soluble salts. Methyl cellulose is dissolved in water at a concentration of 30% and the sintering temperature is held constant at 1100° C. In both sensors, there is a range of the reaction temperature where the response time is minimal. Below the range, the compound oxide of a single perovskite structure cannot be obtained. Higher temperatures result in undesirably larger sizes of the powder. The use of an aqueous solution of water-soluble salts is advantageous in that the constituent elements can uniformly be mixed with one another, so that the perovskite single phase is likely to form even at lower reaction temperatures and that lower reaction temperatures result in finer size of particles.

Figure 11:
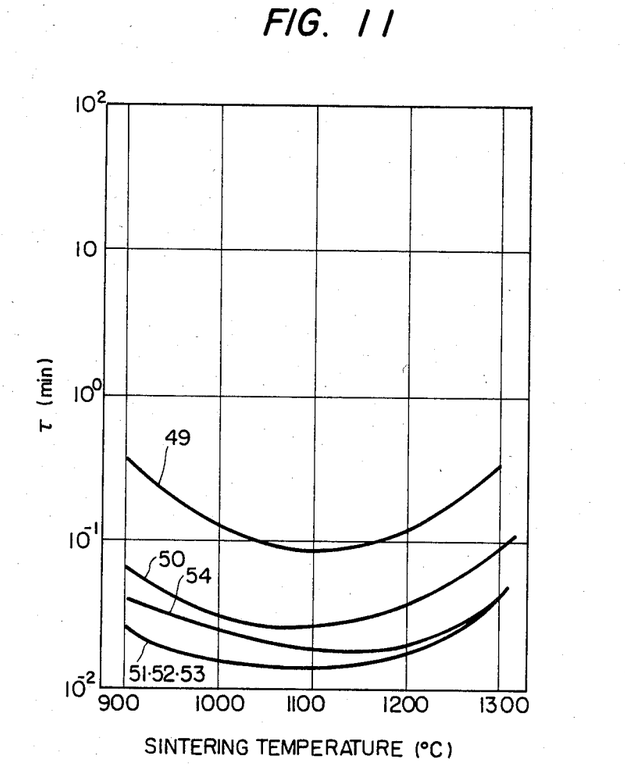
FIG. 11 is a graphical representation of the response time in relation to the variation in sintering temperature.

FIG. 11 shows a relation between the response time and the sintering temperature for different concentrations of methyl cellulose. In the figure, indicated by 49 is a case where 40% of methyl cellulose based on a compound oxide used is added without being dissolved in water, and by 50, 51, 52, 53 and 54 are cases where (10)%, (20)%, (30)%, (40)% and (50)% of methyl cellulose are added and dissolved in water, respectively. In all the cases, the starting powder of the compound oxide of $L_{0.4}Sr_{0.6}Co_{0.8}Fe_{0.2}O_3$ is prepared from an aqueous solution of salts by reaction at 900° C. As is clearly seen from the figure, the responsibility is more excellent in the cases where methyl cellulose is dissolved in water than in the case where methyl cellulose is merely added in the form of a powder. Presumably, this is because the methyl cellulose dissolved in water is uniformly deposited on each particle of the compound oxide, ensuring uniform sintering. The optimum range in amount of methyl cellulose is 20 to 40% based on the compound oxide powder. The reason why the response time becomes poorer when less amounts of methyl cellulose are used is believed as follows: The porosity of the substrate becomes small, so that the diffusion of a gas from outside is impeded. On the contrary, larger amounts result in an excessively greater porosity, thus giving an adverse influence on the sintering of the compound oxide.

Figure 12:
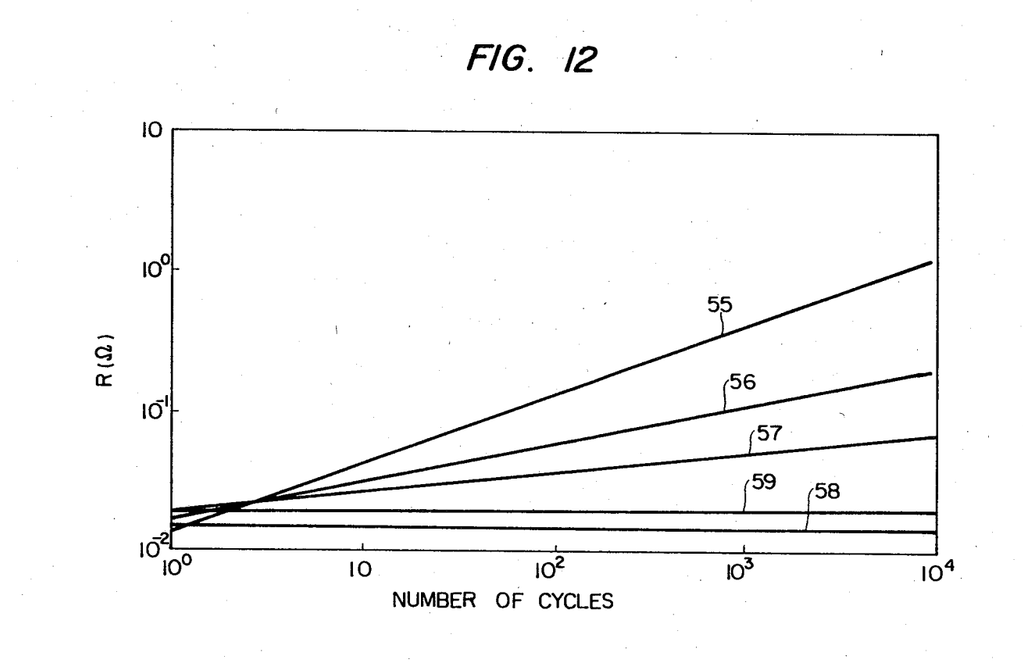
FIG. 12 is a relation between the resistance in an oxidative gas-rich atmosphere and the repeated cycle where the type of atmospheric gas is changed from one to another at intervals, for different materials for metal wire serving as an electrode and lead.

The resistance of the sensor according to the invention has been found to be gradually deteriorated when used repeatedly over a long time. This deterioration can be mitigated when a specific type of metallic wire is used as an electrode and lead attached to the sensor substrate. This is particularly depicted in FIG. 12. That is, a sensor substrate made of $La_{0.35}Sr_{0.65}Co_{0.7}Fe_{0.3}O_3$ is provided and attached with several types of metallic wires as an electrode and lead in a manner shown in FIGS. 2(a) and 2(b). The metallic wires used are made of Pt, Pd, Pd-Au (1:0.3 on a weight basis), Pd-Ag (1:0.3) and Pd-Cu (1:0.3), respectively. The steady state resistance of each sensor in normal air is measured after repetition of a cycle where normal air and the oxygen-lean air (18% $O_2$) are passed over each substrate under conditions indicated with reference to FIGS. 8 and 9. In FIG. 12, indicated by 55 is a sensor using Pt wire, by 56 is a sensor using Pd wire, by 57 is a sensor using Pd-Au alloy wire, by 58 is a sensor using Pd-Ag alloy, and by 59 is a sensor using Pd-Cu alloy. As will be apparent from FIG. 12, the sensors using the Pt and Pd wires gradually increase in resistance when subjected to the repeated cycle of changing the atmospheric gas from normal air to oxygen-lean air but the sensors using the Pd-Ag and Pd-Cu alloy wires show very small variations in resistance. The reason for this is believed partly due to the fact that coefficients of thermal expansion of the substrate and the wires are close to each other. In this connection, however, this is true of the Pd-Au wire, but the sensor using this Pd-Au wire deteriorates in resistance after the repetition of the cycle. Accordingly, it is considered necessary that the wire useful for this purpose is appropriately formed with an oxide layer on the surface thereof. Similar results are obtained when using Pt in combination with Ag or Cu.

What is claimed is:

1. A sensor element which comprises a porous substrate made of a compound oxide of the perovskite type and a pair of electrodes electrically connected to said substrate in a spaced relation with each other, the compound oxide having the formula $A_{1-x}A'_xB_{1-y}B'_yO_3$ in which A represents a trivalent element selected from the group consisting of La, Ce, Pr and Nd, A' represents a divalent element selected from the group consisting of Ca, Sr and Ba, B represents equal amounts of trivalent and tetravalent Co, B' represents (a tetravalent element selected from the group consisting of Fe, Mn, V and Ti, x has a value ranging from 0.6 to 0.95 and y has a value ranging from 0.2 to 0.9 with the proviso that x must equal $\frac{1}{2}(1+y)$.

2. A sensor element according to claim 1, wherein the element A is La and the element A' is Sr.

3. A sensor element according to claim 1, wherein y is in the range of 0.2 to 0.4 when said sensor is to be used in an atmosphere where CO gas is rich and y is 0.9 when said sensor is to be used in an atmosphere where hydrocarbons or $H_2$ is rich.

4. A sensor element according to claim 1, wherein said pair of electrodes are each made of an alloy of Pt or Pd and Ag or Cu.

5. A sensor element of claim 1 connected in series to a power circuit together with an actuator solenoid whereby said actuator solenoid can be worked in response to an abrupt variation in resistance of said sensor element.

* * * * *

UNITED STATES PATENT AND TRADEMARK OFFICE
CERTIFICATE OF CORRECTION

PATENT NO. : 4,601,883

DATED : July 22, 1986

INVENTOR(S) : Satoshi SEKIDO; Hirokazu TACHIBANA and Yoshito NINOMIYA

It is certified that error appears in the above-identified patent and that said Letters Patent is hereby corrected as shown below:

On the title page insert

-- [73] Assignee: Matsushita Electric Industrial Company, Ltd. --

Signed and Sealed this

Seventeenth Day of February, 1987

Attest:

DONALD J. QUIGG

Attesting Officer

Commissioner of Patents and Trademarks